US010907625B2

(12) United States Patent
Oakes et al.

(10) Patent No.: US 10,907,625 B2
(45) Date of Patent: Feb. 2, 2021

(54) SHAPE MEMORY ACTUATOR

(71) Applicant: ViCentra B.V., Utrecht (NL)

(72) Inventors: Timothy William Oakes, Swansea (GB); Joseph Cefai, West Glamorgan (GB)

(73) Assignee: VICENTRA B.V., Utrecht (NL)

( * ) Notice: Subject to any disclaimer, the term of this patent is extended or adjusted under 35 U.S.C. 154(b) by 373 days.

(21) Appl. No.: 15/769,457

(22) PCT Filed: Dec. 12, 2016

(86) PCT No.: PCT/EP2016/080688
§ 371 (c)(1),
(2) Date: Apr. 19, 2018

(87) PCT Pub. No.: WO2017/118539
PCT Pub. Date: Jul. 13, 2017

(65) Prior Publication Data
US 2018/0313346 A1 Nov. 1, 2018

(30) Foreign Application Priority Data
Jan. 6, 2016 (GB) .................. 1600234.7

(51) Int. Cl.
F04B 43/04 (2006.01)
F03G 7/06 (2006.01)
(Continued)

(52) U.S. Cl.
CPC ......... *F04B 43/043* (2013.01); *A61M 5/1452* (2013.01); *A61M 5/14586* (2013.01);
(Continued)

(58) Field of Classification Search
CPC ........ F04B 19/006; F04B 19/22; F04B 23/02; F04B 43/043; F04B 43/0054; F03G 7/065;
(Continued)

(56) References Cited

U.S. PATENT DOCUMENTS 4,586,335 A * 5/1986 Hosoda ................. B25J 18/025
294/86.4
6,522,518 B1 * 2/2003 Barnett .................. H01R 13/24
257/691
(Continued)

FOREIGN PATENT DOCUMENTS

| CN | 102665799 A | 12/2012 |
|---|---|---|
| DE | 100 48 220 A1 | 5/2001 |

(Continued)

OTHER PUBLICATIONS

Jul. 25, 2016 Ukipo Search Report for GB 16 00234.7.
(Continued)

Primary Examiner — William R Carpenter
Assistant Examiner — Larry R. Wilson
(74) Attorney, Agent, or Firm — Hahn Loeser & Parks LLP

(57) ABSTRACT

The invention provides an actuator having a wedge shaped member arranged to move in substantially linear reciprocating motion. A drive member is operatively coupled to the wedge shaped member. The wedge shaped member is arranged to deflect the drive member as the wedge shaped member moves. A shape memory material has a first end electrically connected to a first electrical connection terminal and fixed with respect to the first electrical connection terminal, and a second end electrically connected to the wedge shaped member and fixed with respect to the wedge shaped member. The wedge shaped member is electrically (Continued)

connected to a second electrical connection terminal. The actuator may be used in a pump having a pumping chamber with a membrane the displacement of which changes the pumping chamber volume. The drive member of the actuator is operatively coupled to the pumping chamber membrane. The pump may be used in an infusion system for the infusion of a liquid therapeutic product.

22 Claims, 11 Drawing Sheets

(51) Int. Cl.
   *F04B 19/22* (2006.01)
   *F04B 19/00* (2006.01)
   *A61M 5/145* (2006.01)
   *F04B 43/00* (2006.01)
   *F04B 23/02* (2006.01)
   *A61M 5/158* (2006.01)

(52) U.S. Cl.
   CPC ............ *F03G 7/065* (2013.01); *F04B 19/006* (2013.01); *F04B 19/22* (2013.01); *F04B 23/02* (2013.01); *F04B 43/0054* (2013.01); *A61M 5/158* (2013.01); *A61M 2005/1585* (2013.01); *A61M 2205/0244* (2013.01); *A61M 2205/0266* (2013.01); *A61M 2205/3584* (2013.01); *A61M 2205/502* (2013.01); *A61M 2205/8206* (2013.01); *F05C 2251/06* (2013.01); *F05C 2251/08* (2013.01)

(58) Field of Classification Search
   CPC ............ F05C 2251/08; A61M 5/1452; A61M 5/14586; A61M 5/158; A61M 2005/1585; A61M 2205/0244; A61M 2205/0266; A61M 2205/3584; A61M 2205/502; A61M 2205/8206
   See application file for complete search history.

(56) References Cited

U.S. PATENT DOCUMENTS

| | | | |
|---|---|---|---|
| 6,656,158 | B2 | 12/2003 | Mahoney et al. |
| 2003/0199824 | A1 | 10/2003 | Mahoney et al. |
| 2003/0229310 | A1 | 12/2003 | Flaherty et al. |
| 2010/0308689 | A1* | 12/2010 | Rahman ................. E21B 23/00 310/328 |
| 2015/0051547 | A1* | 2/2015 | Cefai .................... F04B 43/043 604/135 |

FOREIGN PATENT DOCUMENTS

| | | |
|---|---|---|
| GB | 2500646 A | 10/2013 |
| JP | 2006 038931 A | 2/2006 |
| WO | WO 2002/05876 A2 | 1/2002 |
| WO | WO 2009/118553 A1 | 10/2009 |

OTHER PUBLICATIONS

Feb. 21, 2017 ISR for PCT/EP2016/080688.
Feb. 21, 2017 Written Opinion of ISA for PCT/EP2016/080688.
English translation of Jun. 3, 2019 Office Communication in connection with CN 2016 8007 8305.1.

* cited by examiner ly 2017
SHAPE MEMORY ACTUATOR

The present application is a § 371 submission of international application no. PCT/EP2016/080688, filed 12 Dec. 2016 and published in the English language on 13 Jul. 2017 with publication no. WO 2017/118539 A1, which claims the benefit of the filing date of GB 16 00234.7 filed 6 Jan. 2016.

FIELD OF THE INVENTION

The present invention relates to a shape memory actuator for a pump, a pump, and an infusion system including the pump for the infusion of a liquid therapeutic product.

BACKGROUND OF THE INVENTION

A variety of actuators are known in the art for providing the mechanical displacement required in devices designed for pumping fluids.

Shape memory alloy (SMA) has been proposed as a suitable material for an actuator of the type described above and a number of devices based on this mechanical driver have been described. SMA mechanical drivers can be suitable for micro-pump applications due to their high force-to-weight ratio, mechanical simplicity, compactness, and silent, clean operation. SMA mechanical drivers also provide cost effective solutions for the design of short term use, disposable products that are easy to manufacture, that are produced in very large numbers and at a cost effective price.

U.S. Pat. No. 6,656,158 describes a fluid dispensing device that uses a SMA to move a pawl against a toothed gear system attached to the fluid dispensing portion of the device. Every time the SMA is activated the pawl moves against the gear and indexes the gear from its first position to a second position. The gear does not return to its first position. This device overcomes a known disadvantage in the lack of accuracy frequently found in the use of SMA, by using the SMA to move an accurately formed gear system. However, the device described in U.S. Pat. No. 6,656,158 uses a relatively long length of SMA wire which has significant electrical resistance and therefore impacts battery life of the device. Furthermore the SMA wire runs over pulleys which reduces the life of the SMA wire due to wear cause by slip on the pulleys, and the pulley arrangement is complex leading to a high cost of goods.

SUMMARY OF THE INVENTION

A first aspect of the invention provides an actuator for a pump, the actuator comprising: a wedge shaped member arranged to move in substantially linear reciprocating motion, a drive member operatively coupled to the wedge shaped member, the wedge shaped member being arranged to deflect the drive member as the wedge shaped member moves, a shape memory material having a first end and a second end, the first end is electrically connected to a first electrical connection terminal and is fixed with respect to the first electrical connection terminal, the second end is electrically connected to the wedge shaped member and is fixed with respect to the wedge shaped member, and the wedge shaped member is electrically connected to a second electrical connection terminal.

A second aspect of the invention provides a pump comprising: a pumping chamber having a volume with an inlet, an outlet, and a membrane the displacement of which changes the pumping chamber volume; and an actuator according to the first aspect, wherein the drive member is operatively coupled to the pumping chamber membrane.

A third aspect of the invention provides an infusion system for the infusion of a liquid therapeutic product, comprising a reservoir for storing the liquid therapeutic product, and the pump according to the second aspect.

The infusion system comprising the fluid delivery system may be adapted for the infusion of one of a variety of liquid therapeutic products. In one application the infusion system is an insulin infusion system for continuous subcutaneous insulin infusion therapy.

The invention is advantageous in that the shape memory material may extend substantially linearly between first and second ends thereof and cause reciprocating linear motion of the wedge shaped member to move the drive member. The wedge shaped member is electrically conductive and forms part of the electrical circuit between the first electrical connection terminal and the second electrical connection terminal. The wedge shaped member may provide a high degree of movement accuracy yet the actuator has a simple design with few parts, which can be manufactured without high tolerance requirements, and assembled so as to cause minimal wear on the shape memory material. In this way the actuator may be manufactured inexpensively yet provide a high degree of movement accuracy making it suitable for use in, e.g. a fluid delivery system for the infusion of a liquid therapeutic product.

The wedge shaped member may be moveable with respect to the drive member.

The wedge shaped member and the drive member may be arranged to convert the reciprocating substantially linear motion of the wedge shaped member along a first axis to reciprocating substantially linear motion of the drive member along a second axis substantially perpendicular to the first axis.

The wedge shaped member may have a first surface, a second surface, and a third surface between the first surface and the second surface, wherein the third surface is inclined with respect to the first surface and the second surface.

The actuator may include a lever rotatable about a pivot point, and the drive member may be operatively coupled to the lever.

The lever may have a distal end opposite the pivot point, and the distal end of the lever may be operatively coupled to the wedge shaped member.

The distal end of the lever may have an inclined surface arranged for sliding contact along the inclined surface of the wedge shaped member. Alternatively the lever may have a taper providing a point for sliding contact along the inclined surface of the wedge shaped member.

The actuator may have a first biasing element for biasing the lever towards the wedge shaped member about the pivot point. The biasing element may be a spring, e.g. a compression spring, or a membrane in tension.

The lever may provide the electrical connection between the wedge shaped member and the second electrical connection terminal.

The actuator may have a runner, wherein the wedge shaped member is arranged to move in sliding contact with respect to the runner.

The runner may provide the electrical connection between the wedge shaped member and the second electrical connection terminal.

The actuator may have a second biasing element for biasing the wedge shaped member to a first position. The second biasing element may provide the electrical connection between the wedge shaped member and the second electrical connection terminal. The second biasing element may be a coil spring, and the shape memory material may pass through the eye of the coil.

The shape memory material may have a first shape corresponding to a first position of the wedge shaped member, and a second shape corresponding to a second position of the wedge shaped member.

The shape memory material may be a shape memory alloy. The shape memory alloy may be a resistance heating shape memory alloy, such as a Nitinol alloy (Nickel-Titanium in approximately a 1:1 ratio). The shape memory material may be formed as a wire, e.g. a muscle wire. The wire may be substantially straight between the first end and the second end thereof.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
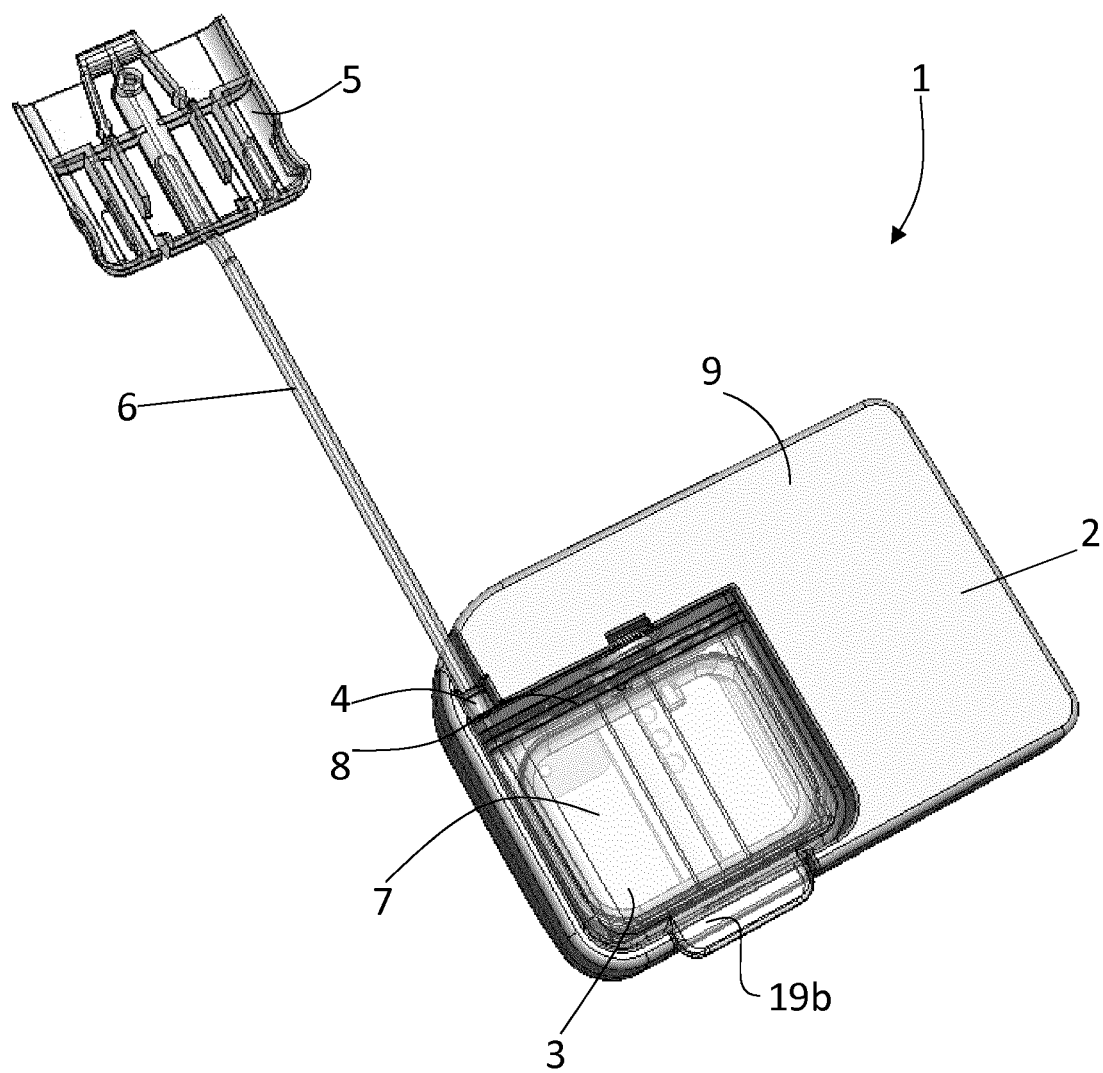
FIG. 1 illustrates a wearable part of an external infusion system.

FIG. 1 shows the wearable part of an external infusion system 1 for the continuous subcutaneous infusion of insulin into the human body through repetitive small pulses of infusion. The infusion system 1 comprises a pump part 2, a cartridge 3 having an outlet port 4 connected to an infusion set 5 via an infusion tube 6.

The infusion set 5 includes a subcutaneous cannula and an adhesive mount for adhering the infusion set to the patient's skin. The cannula is typically made of flexible plastic so as not to cause discomfort for the patient during use. The infusion set is typically installed into a spring loaded insertion device together with a steel needle surrounding the cannula. Upon insertion, the steel needle is removed leaving the cannula in place. Alternative infusion sets, which may replace the infusion set shown in FIG. 1, comprise a steel needle instead of the cannula.

Depending on the desired positioning of the pump part 2 with respect to the infusion set 5 during use the length of the infusion tube 6 may be longer or shorter than that shown in FIG. 1, and indeed the infusion set 5 may be coupled directly to the output port 4 of the pump where close coupling of the infusion set 5 and the pump part 2 is desired, thereby avoiding the need for the flexible infusion tube 6.

The cartridge 3 includes a reservoir 7 for storing a supply of insulin and a pumping chamber 8. The pump part 2 contains an actuator, a rechargeable battery power supply and control electronics for controlling the actuator.

The cartridge 3 is removably attachable to a housing 9 of the pump part 2 such that when the cartridge 3 is attached to the housing 9 a drive member of the actuator is operatively coupled to the pumping chamber 8 for delivering a supply of insulin from the reservoir 7 to the outlet port 4 and into the infusion set 5 via the infusion tube 6.

Figure 2:
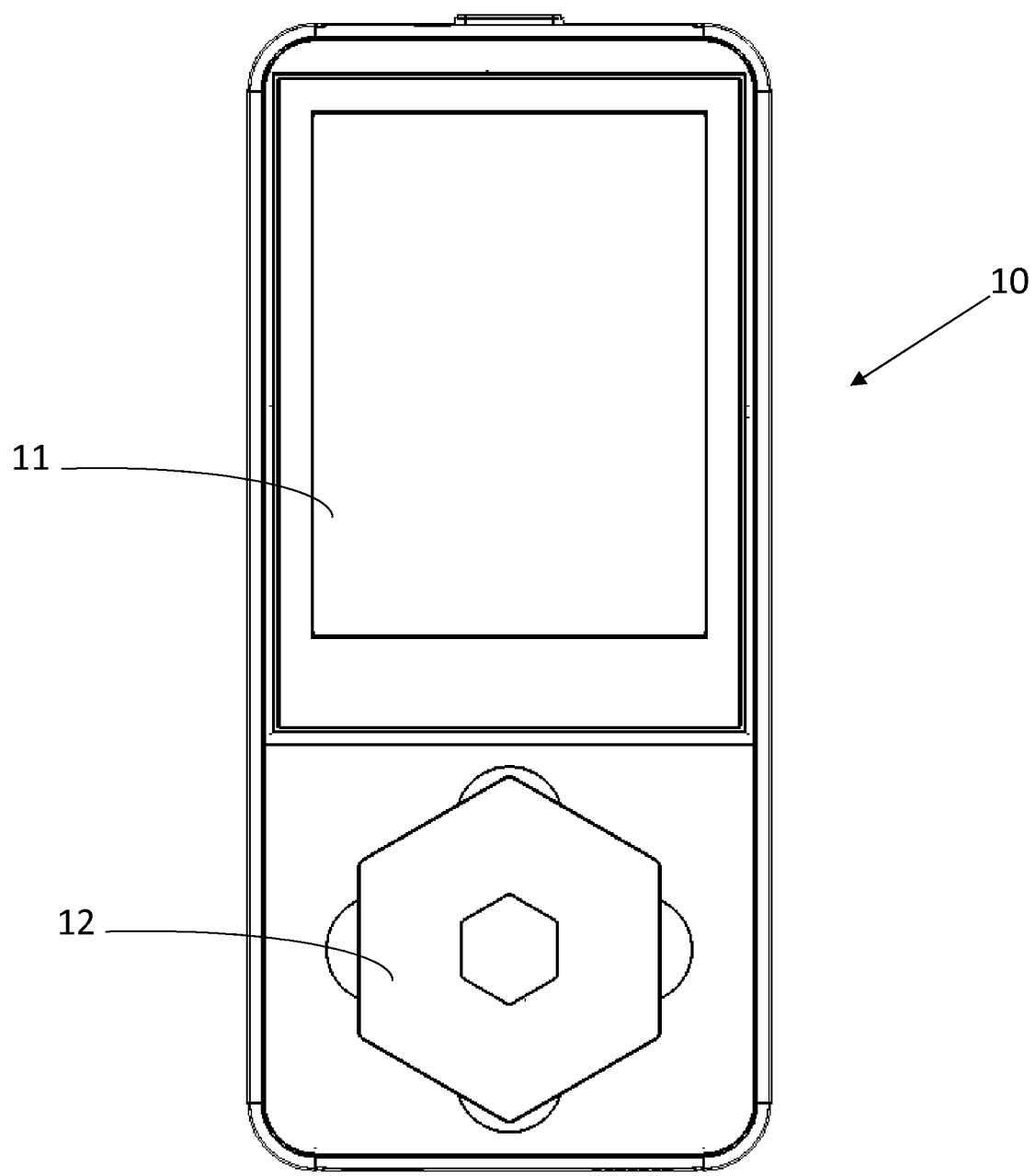
FIG. 2 illustrates a handset of the infusion system for wireless communication with the wearable part.

The control electronics of the pump part 2 includes a transceiver for wireless communication with a user control handset 10 shown in FIG. 2. The handset 10 also includes a transceiver for wireless communication with the pump part 2. The wireless communication may be via Bluetooth™ or other radio frequency near field communication means. The handset 10 includes a graphical user interface 11 and a tactile user interface 12. The handset 10 enables a user to perform the following functions:

Define and store basal profiles;
Transfer an active basal profile to the pump 2;
Define and transmit a bolus request to the pump 2;
Define and transmit a temporary basal to the pump 2;
View a graphical recommendation of a bolus based on glucose readings from a separate blood glucose meter or entered manually following a blood glucose meter reading from a separate blood glucose meter (not shown);
View graphically pump performance over time;
Request the current status of the pump 2 (including what insulin delivery is currently in progress, battery status, alarm conditions, insulin reservoir level, etc).

The handset 10 is also enabled for internet connectivity, e.g. by a wireless radio connection such as Bluetooth™ or Wi-Fi between the handset and remote internet connected devices. The internet connectivity enables two-way patient support either directly or via an intermediate internet connected device such as a PC, laptop or mobile device.

Figure 3:
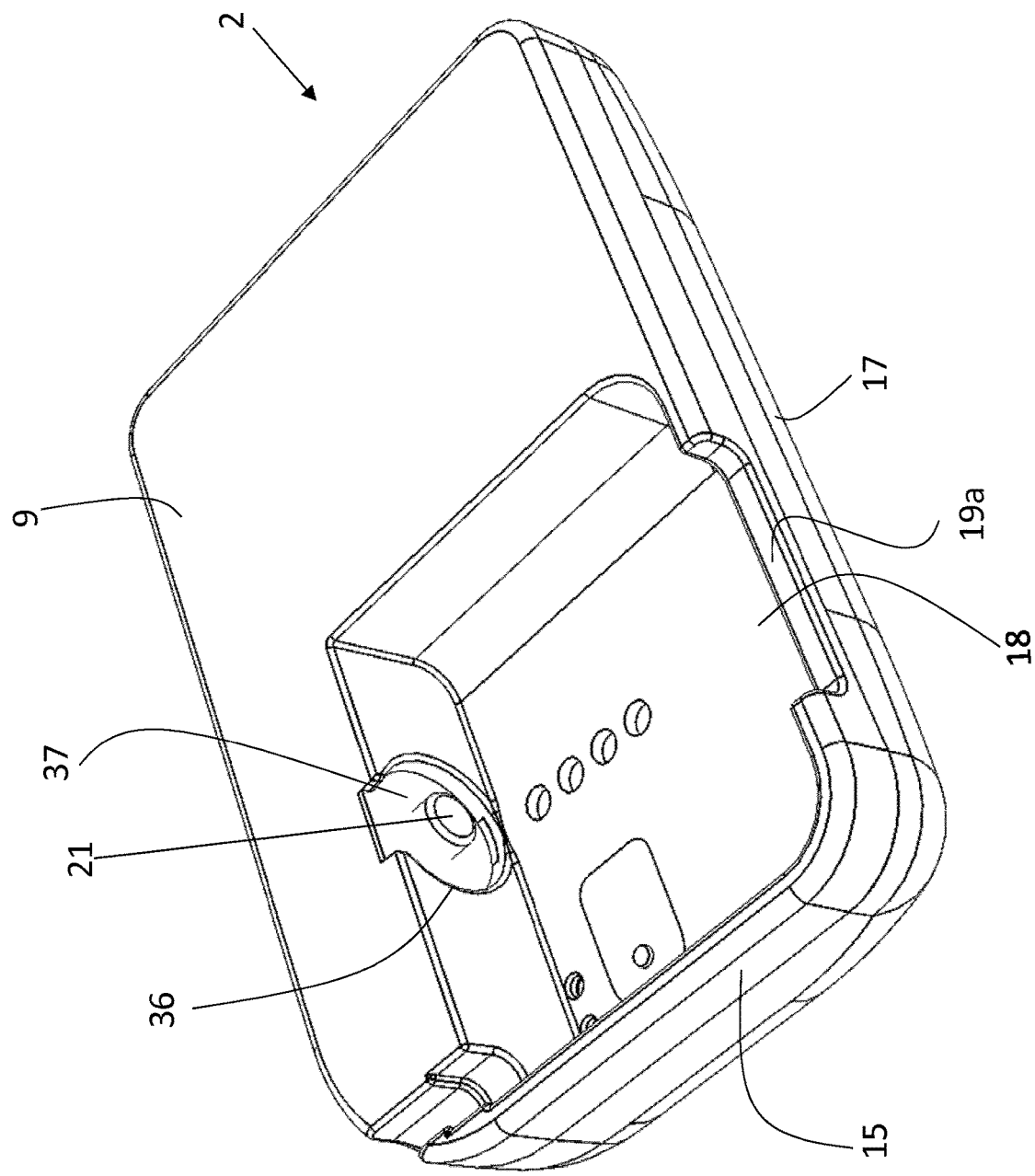
FIG. 3 illustrates a durable pump part of the infusion system.
Figure 4:
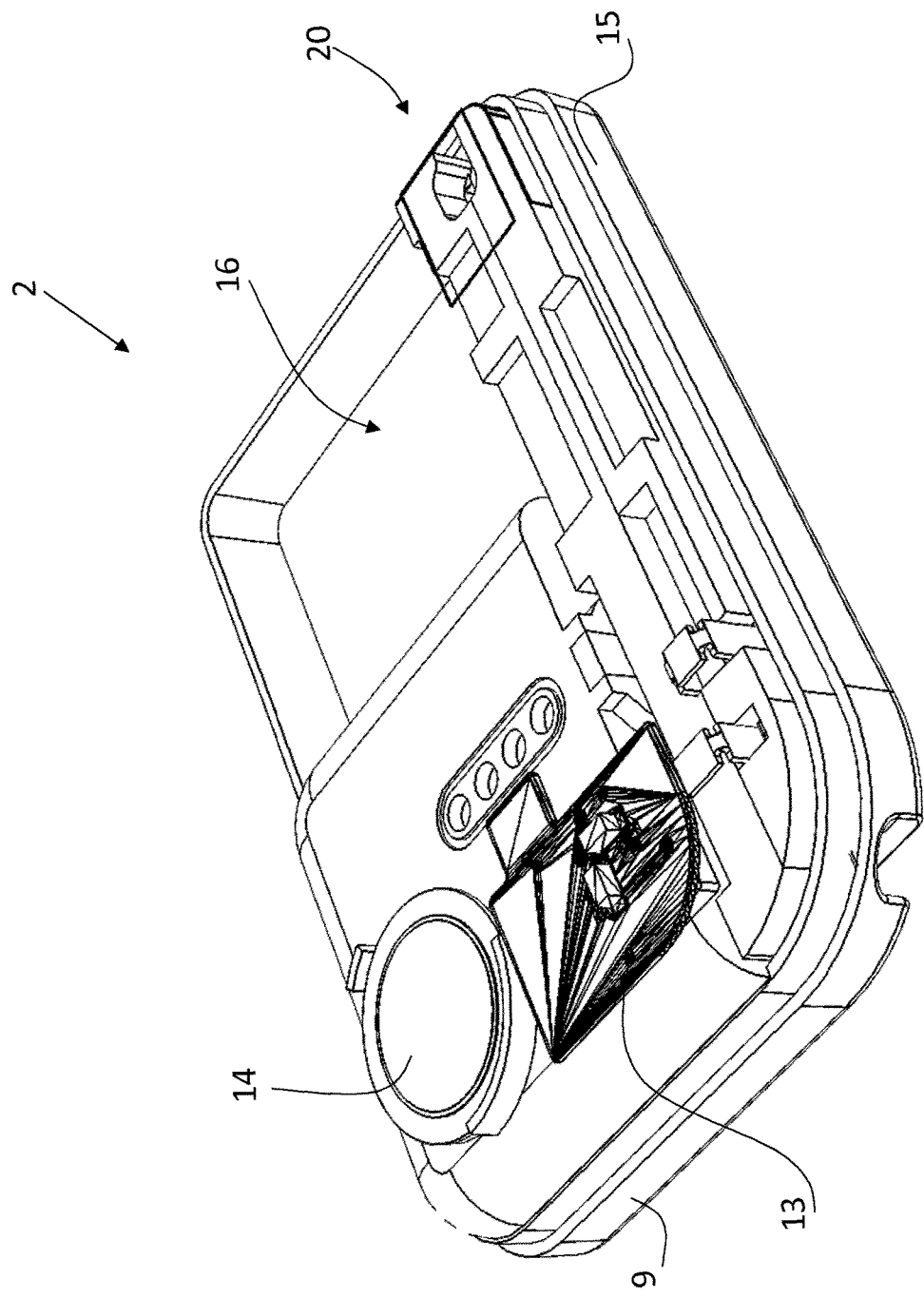
FIG. 4 illustrates the durable pump part with its cover removed.
Figure 5:
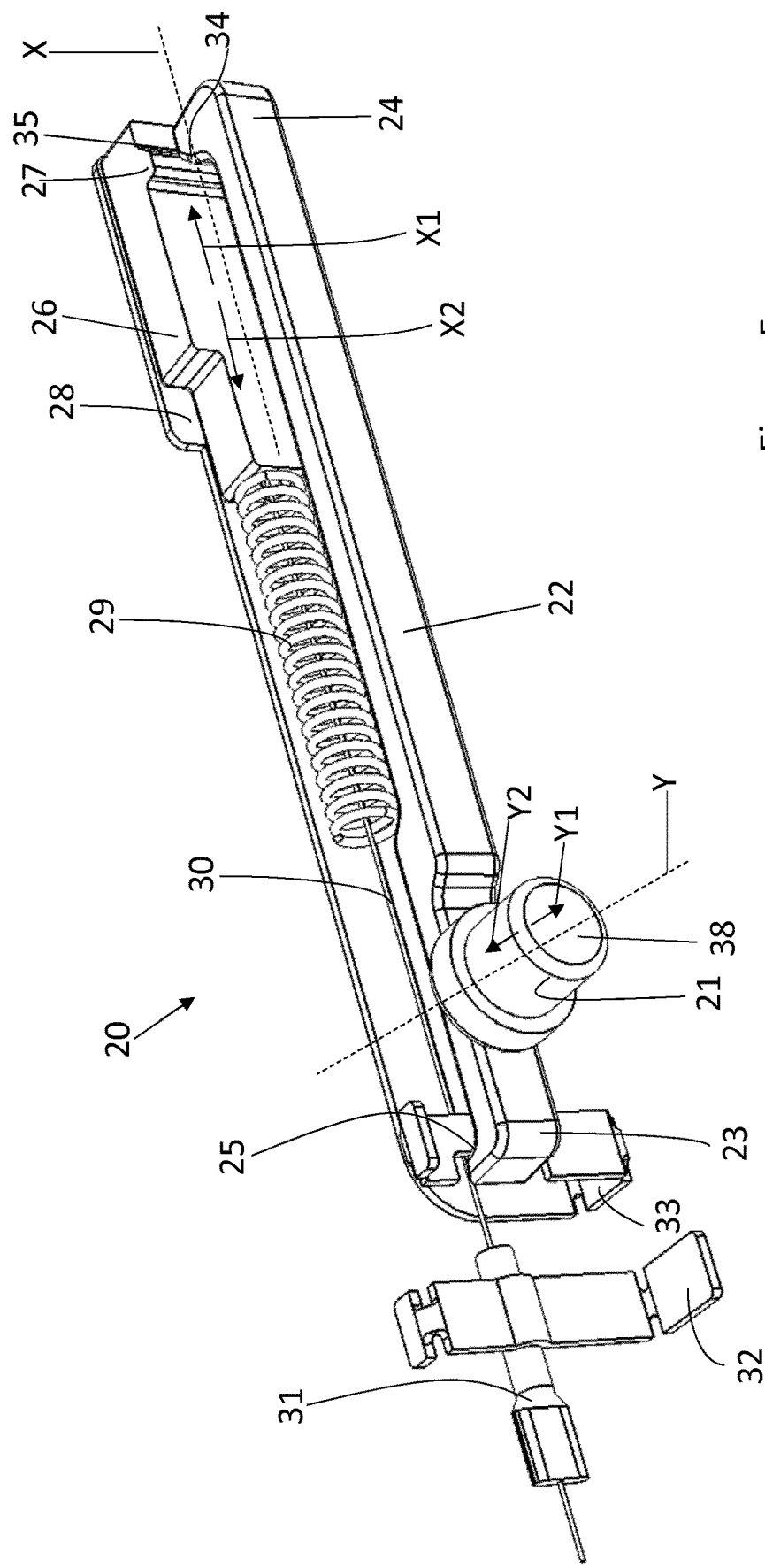
FIG. 5 shows a cutaway view of the actuator for the pump.

Turning next to FIGS. 3 to 5 the pump part 2 will now be described in detail. As shown in FIGS. 3 and 4 the pump part 2 includes an actuator 20 for driving a drive member 21 in reciprocating motion. The housing 9 also contains a printed circuit board 13 carrying the control electronics, a piezoelectric sounder 14, a chassis 15 for supporting the actuator 20, the PCB 13, the piezo-electric sounder 14 and defining a battery holder 16 for receiving a rechargeable battery (not shown). In FIG. 4 a top cover 17 (visible in FIG. 3) has been removed for clarity. As best shown in FIG. 3, the chassis 15 defines a recess 18 for receiving the cartridge 3. In FIG. 3 the pump 2 is shown with the cartridge 3 removed. The pump part 2 and the cartridge 3 have cooperating retaining features 19a, 19b for the secure retention and ready removal of the cartridge 3 from the pump part 2 using a snap fit type connection.

FIG. 5 illustrates the actuator 20 in detail. The actuator 20 includes a lever 22 having a proximal end 23 and a distal end 24 opposite the proximal end 23. The lever 22 is rotatable about a pivot point 25 at its proximal end 23. Drive member 21 is formed as a generally cylindrical piston operatively coupled to the lever 22. The drive member 21 is disposed spaced from the pivot point 25 and is disposed nearer the proximal end 23 than to the distal end 24 of the lever 22. The actuator 20 further comprises a slider 26 having a wedge shaped member 27. The slider 26 is in sliding contact with a runner 28. The slider 26 is in sliding contact with the runner 28 and moves with respect to the runner 28 along an axis X. A compression spring 29 biases the slider 26 in the direction of arrow X1 against an end stop (not shown) to a first position.

A shape memory alloy actuator 30, which in the illustrated embodiment is a Nitinol muscle wire, is securely retained at one end to the slider 26 and is securely retained at its other end by a crimp assembly 31. The crimp assembly 31 is electrically conductive and is electrically connected to a first terminal 32. The slider 26 is electrically conductive and forms an electrically conductive sliding contact with the runner 28. The runner 28 is electrically connected to a second terminal 33.

The distal end 24 of the lever 22 has an inclined surface 34 which contacts an inclined surface 35 of the wedge shaped member 27. The inclined surfaces 34, 35 are inclined with respect to axis X. In FIG. 5 the actuator 20 is depicted in a first position in which the slider 26 is biased in the direction of arrow X1 to the first position in which the lever 22 is pivoted about pivot point 25 away from the runner 28. A unique property of a Nitinol shape memory alloy is its super elasticity. Under the action of the compression spring 29 the Nitinol muscle wire 30 is deformed by elastic strain such that the length of the muscle wire 30 between its crimped ends is significantly longer than in its un-deformed, as manufactured, state.

When an electric current is passed between the terminals 32 and 33 an electrical connection is made via the crimp assembly 31, the Nitinol muscle wire 30, the slider 26, and the runner 28. Due to the small diameter of the Nitinol muscle wire 30, the Nitinol muscle wire 30 undergoes resistance heating which causes the Nitinol muscle wire 30 to heat up and recover its original, un-deformed shape which shortens the length of the Nitinol wire 30 between its crimped ends, thus moving the slider 26 in the direction of arrow X2 against the bias of the compression spring 29.

This movement of the slider 26 causes relative sliding movement of the inclined surfaces 35 and 34 of the wedge shaped member 27 and the distal end 24 of the lever 22 such that the lever 22 pivots about the pivot point 25 to move the lever 22 towards the runner 28. This in turn moves the drive member 21 in the direction of arrow Y2 along axis Y which lies substantially perpendicular to axis X.

When current ceases to flow between the terminals 32 and 33 the resistance heating of the Nitinol muscle wire 30 is stopped and as the muscle wire cools the compression spring 29 causes the muscle wire 30 to once again deform under super elasticity and the slider 26 moves in the direction of arrow X1, causing rotation of the lever 22 about pivot point 25 and corresponding movement of the drive member 21 in the direction of arrow Y1.

In this way the cyclic heating and cooling of the Nitinol muscle wire 30, by switching on and off an electric current between the terminals 32 and 33, causes the drive member 21 to move along axis Y in reciprocating motion in the direction of arrows Y1 and Y2. The selective opening and closing of the circuit between the terminals 32 and 33 is effected by the control electronics of the printed circuit board 13 with the electrical energy being provided by the battery (not shown).

Reverting to FIG. 3, showing the pump part 2 with the cartridge 3 removed, the drive member 21 can been seen in an aperture 36 in the housing 9. The drive member 21 is covered by a membrane 37. The membrane 37 is an elastomeric membrane stretched over a head 38 of the drive member 21. The membrane 37 performs two functions. Firstly, membrane 37 ensures the housing 9 is fluid tight to protect the electrical components therein. Secondly, membrane 37 provides a biasing function to the drive member 21 to bias the drive member 21 in the direction of arrow Y2. The membrane 37 applies a force in the direction of arrow Y2 throughout the full range of reciprocating motion of the drive member 21. The stretched membrane 37 may achieve a tension of approximately 2 Newtons. In other embodiments the drive member 21 is biased by another component, such as a spring in the actuator 20 or a membrane in the cartridge 3 for example, which may be used in addition to or instead of the biasing function of the membrane 37.

When the Nitinol muscle wire 30 is heated to cause the Nitinol muscle wire to contract and move the slider 26 in the direction of arrow X2, relative sliding movement between the inclined surfaces 34 and 35 occurs and the membrane 37 urges the drive member 21 to move in the direction of arrow Y2 forcing the lever 22 to pivot about pivot point 25. In this way the membrane 37 forms a part of the actuator 20. When the Nitinol muscle wire 30 cools down and the slider 26 under the restoring force of the spring 29 returns to the first position against the end stop (not shown) the drive member 21 is in its fully extended position having moved in the direction of arrow Y1 so as to stretch the membrane 37 to its full extent.

Figure 6:
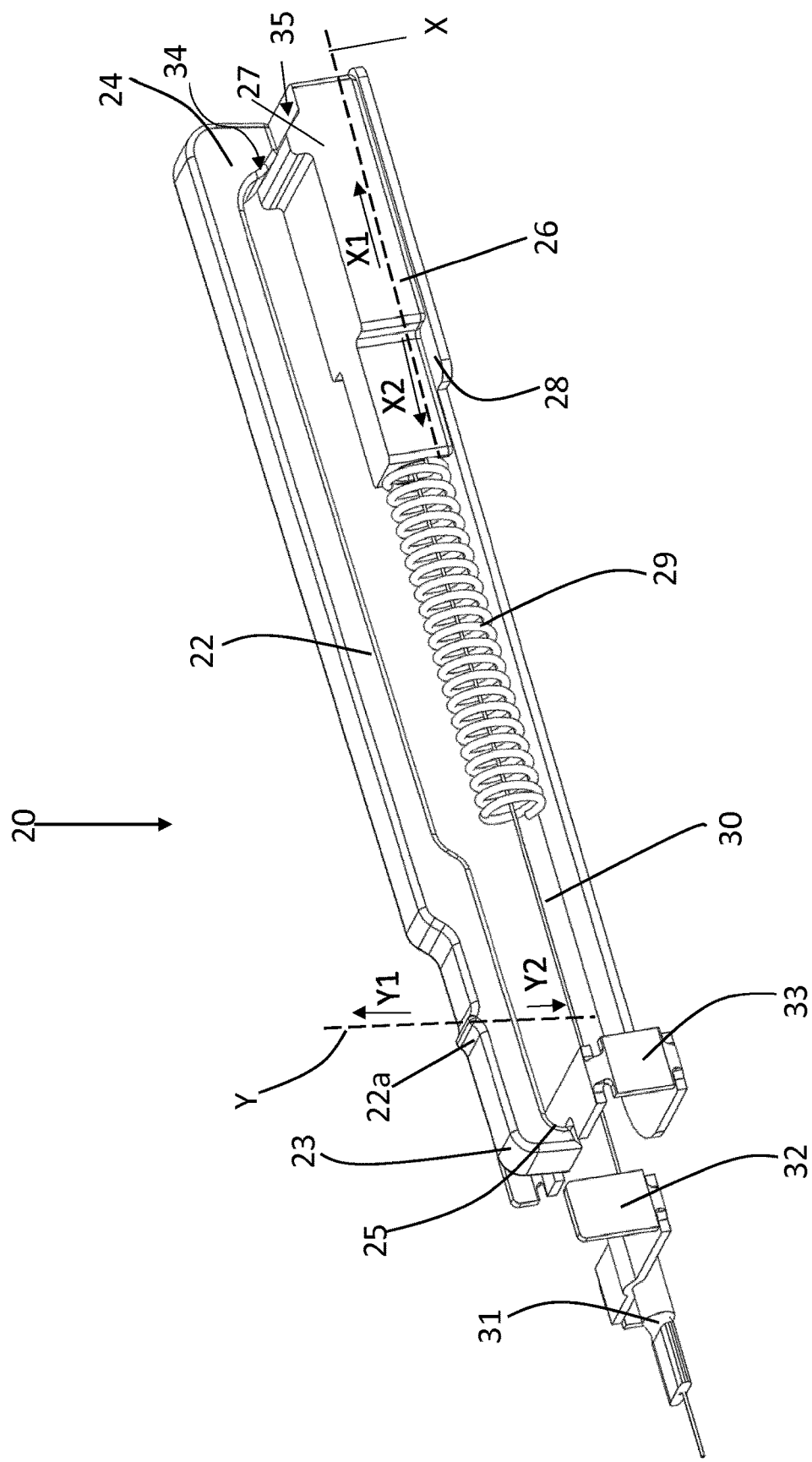
FIG. 6 shows another view of the actuator with the drive member removed.

FIG. 6 shows another view of the actuator 20 with the drive member 21 removed to reveal a drive point 22a of the lever 22. The drive point 22a is formed as a ridge protruding from the lever 22 disposed spaced from the pivot point 25 and nearer the proximal end 23 than to the distal end 24 of the lever 22. The underside of the drive member 21 has a recess for engaging with the drive point 22a to restrict lateral movement of the drive member 21 with respect to the lever 22 but permitting rotation of the drive member 21 through small angles relative to the lever 22 during cycling actuation of the actuator 20.

Figure 7:
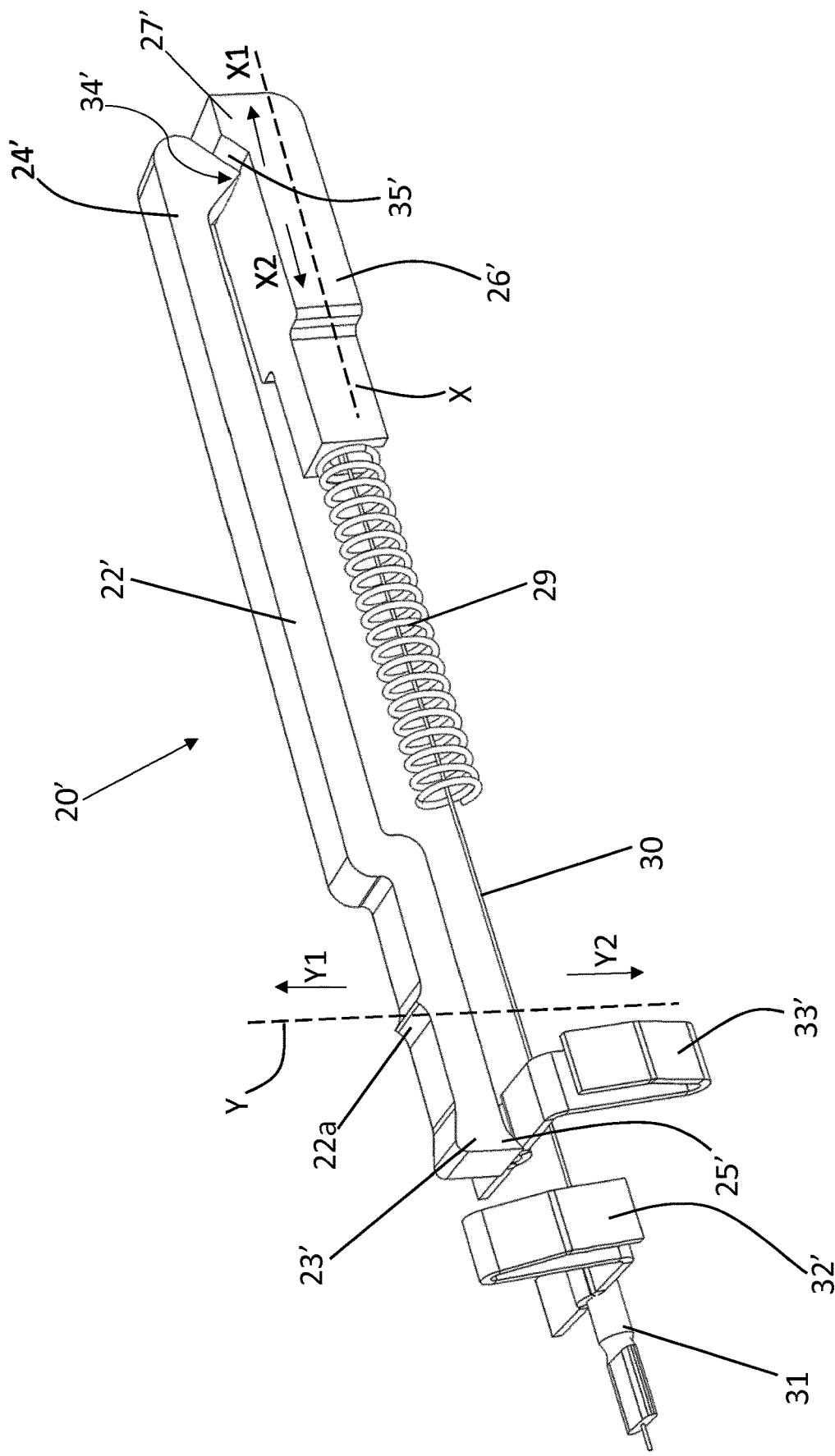
FIG. 7 shows another embodiment of an actuator for the pump.

FIG. 7 shows a first alternative embodiment of the actuator 20' for use in the pump part 2 described above. In this alternative embodiment of the actuator 20' like reference numerals have been used to denote like parts with the above described embodiment, and like reference numerals but with a prime suffix (') have been used to denote similar parts with the above described embodiment. Unless otherwise stated the features and functions of the actuator components are the same as in the above described embodiment.

The actuator 20' includes a lever 22' having a proximal end 23' and a distal end 24' opposite the proximal end 23'. The lever 22' is rotatable about a pivot point 25' at its proximal end 23' and has a drive point 22a for engaging the drive member 21 (not shown in FIG. 7). The drive point 22a is disposed spaced from the pivot point 25' and nearer the proximal end 23' than to the distal end 24' of the lever 22'.

The actuator 20' further comprises a slider 26' having a wedge shaped member 27'. The slider 26' moves along an axis X. A compression spring 29 biases the slider 26' in the direction of arrow X1 against an end stop (not shown) to a first position.

A shape memory alloy actuator 30, which in the illustrated embodiment is a Nitinol muscle wire, is securely retained at one end to the slider 26' and is securely retained at its other end by a crimp assembly 31. The crimp assembly 31 is electrically conductive and is electrically connected to a first terminal 32'. The slider 26' and the lever 22' are each electrically conductive and the distal end 24' of the lever 22' is in electrical and physical contact with the wedge shaped member 27'. The pivot point 25' is electrically connected to a second terminal 33'.

The distal end 24' of the lever 22' has an inclined surface 34' which contacts an inclined surface 35' of the wedge shaped member 27'. The inclined surfaces 34', 35' are inclined with respect to axis X. In FIG. 7 the actuator 20' is depicted in a first position in which the slider 26' is biased in the direction of arrow X1 to the first position in which the lever 22' is pivoted about pivot point 25' towards the slider 26'. Under the action of the compression spring 29 the Nitinol muscle wire 30 is deformed by elastic strain such that the length of the muscle wire 30 between its crimped ends is significantly longer than in its un-deformed, as manufactured, state.

When an electric current is passed between the terminals 32' and 33' an electrical connection is made via the crimp assembly 31, the Nitinol muscle wire 30, the slider 26', and the lever 22'. Due to the small diameter of the Nitinol muscle wire 30, the Nitinol muscle wire 30 undergoes resistance heating which causes the Nitinol muscle wire 30 to heat up and recover its original, un-deformed shape which shortens the length of the Nitinol wire 30 between its crimped ends, thus moving the slider 26' in the direction of arrow X2 against the bias of the compression spring 29.

This movement of the slider 26' causes relative sliding movement of the inclined surfaces 35' and 34' of the wedge shaped member 27' and the distal end 24' of the lever 22' such that the lever 22' pivots about the pivot point 25' to move the lever 22 away from the slider 26'. This in turn moves the drive member 21 in the direction of arrow Y1 along axis Y which lies substantially perpendicular to axis X.

When current ceases to flow between the terminals 32' and 33' the resistance heating of the Nitinol muscle wire 30 is stopped and as the muscle wire cools the compression spring 29 causes the muscle wire 30 to once again deform under super elasticity and the slider 26' moves in the direction of arrow X1, causing rotation of the lever 22' about pivot point 25' and corresponding movement of the drive member 21 in the direction of arrow Y2.

It is therefore apparent that due to the differing orientations of the inclined surfaces 34', 35' of the actuator 20' as compared with the inclined surfaces 34, 35 of the actuator 20 that the displacement of the drive member 21 will be in the opposite sense between the two embodiments. That is to say, when electric current ceases to flow in the Nitinol muscle wire 30 the drive member 21 is in its fully retracted position in the direction of Y2 in the embodiment of the actuator 20' of FIG. 7, whereas when electric current ceases to flow in the Nitinol muscle wire 30 the drive member 21 is in its fully extended position in the direction of Y1 in the embodiment of the actuator 20 of FIGS. 5 and 6.

When the actuator 20' is installed in the pump part 2, the membrane 37 provides a biasing function to the drive member 21 to bias the drive member 21 in the direction of arrow Y2. The membrane 37 applies a force in the direction of arrow Y2 throughout the full range of reciprocating motion of the drive member 21. When the Nitinol muscle wire 30 cools down and the slider 26' under the restoring force of the spring 29 returns to the first position against the end stop (not shown) the membrane 37 urges the drive member 21 to move in the direction of arrow Y2 forcing the lever 22 to pivot about pivot point 25. In this way the membrane 37 forms a part of the actuator 20'. When the Nitinol muscle wire 30 is heated to cause the Nitinol muscle wire to contract and move the slider 26' in the direction of arrow X2, relative sliding movement between the inclined surfaces 34' and 35' occurs forcing the lever 22' to pivot about pivot point 25' and urging the drive member 21 to move in the direction of arrow Y1 to its fully extended position and stretching the membrane 37 to its full extent.

Figure 8:
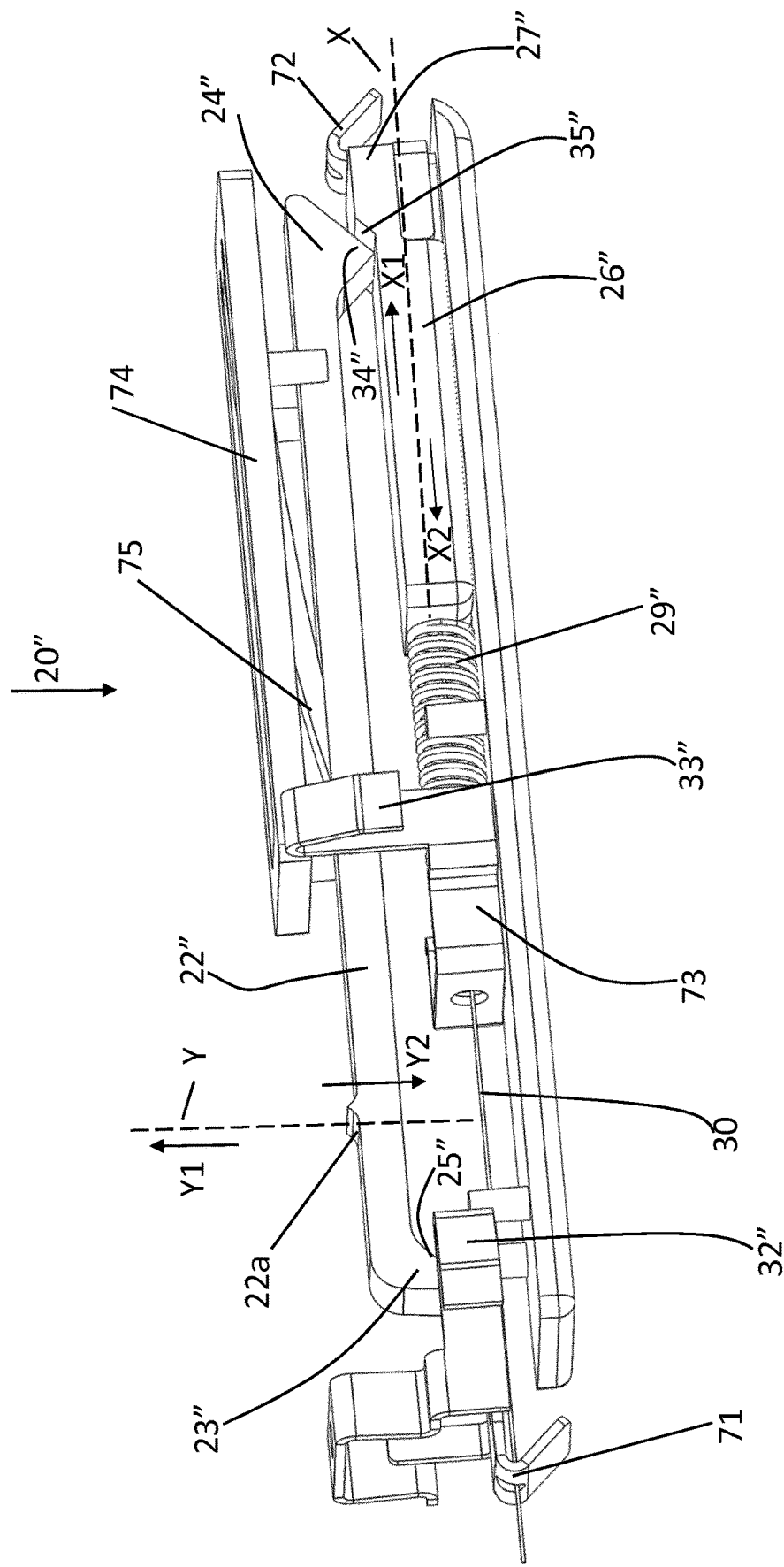
FIG. 8 shows a yet further embodiment of an actuator for the pump.

FIG. 8 shows a second alternative embodiment of the actuator 20" for use in the pump part 2 described above. In this alternative embodiment of the actuator 20" like reference numerals have been used to denote like parts with the above described embodiment, and like reference numerals but with a double prime suffix (") have been used to denote similar parts with the above described embodiment. Unless otherwise stated the features and functions of the actuator components are the same as in the above described embodiment.

The actuator 20" includes a lever 22" having a proximal end 23" and a distal end 24" opposite the proximal end 23". The lever 22" is rotatable about a pivot point 25" at its proximal end 23" and has a drive point 22a for engaging the drive member 21 (not shown in FIG. 8). The drive point 22a is disposed spaced from the pivot point 25" and nearer the proximal end 23" than to the distal end 24" of the lever 22".

The actuator 20" further comprises a slider 26" having a wedge shaped member 27". The slider 26" moves along an axis X. A compression spring 29" biases the slider 26" in the direction of arrow X1 against an end stop (not shown) to a first position.

A shape memory alloy actuator 30, which in the illustrated embodiment is a Nitinol muscle wire, is securely retained at one end to a first electrical connector 71 and is securely retained at its other end to a second electrical connector 72. The first electrical connector 7 is electrically connected to a first terminal 32". The slider 26" and the compression spring 29" are each electrically conductive. The second electrical connector 72 is attached in electrical contact to move with the slider 26". The compression spring 29" is constrained between the slider 26" and a third electrical connector 73. The third electrical connector is electrically connected to a second terminal 33". The Nitinol muscle wire passes through an aperture in the third electrical connector 73 and through a cut out in the slider 26" so as not to make direct electrical contact with the third electrical connector 73 or the slider 26".

The distal end 24" of the lever 22" has an inclined surface 34" which contacts an inclined surface 35" of the wedge shaped member 27". The inclined surfaces 34", 35'" are inclined with respect to axis X. In FIG. 8 the actuator 20" is depicted in a first position in which the slider 26" is biased in the direction of arrow X1 to the first position in which the lever 22" is pivoted about pivot point 25" towards the slider 26". Under the action of the compression spring 29" the Nitinol muscle wire 30 is deformed by elastic strain such that the length of the muscle wire 30 between its ends is significantly longer than in its un-deformed, as manufactured, state.

When an electric current is passed between the terminals 32" and 33" an electrical connection is made via the first electrical connector 71, the Nitinol muscle wire 30, the second electrical connector 72, the slider 26", the compression spring 29" and the third electrical connector 73. Due to the small diameter of the Nitinol muscle wire 30, the Nitinol muscle wire 30 undergoes resistance heating which causes the Nitinol muscle wire 30 to heat up and recover its original, un-deformed shape which shortens the length of the Nitinol wire 30 between its crimped ends, thus moving the slider 26" in the direction of arrow X2 against the bias of the compression spring 29".

This movement of the slider 26" causes relative sliding movement of the inclined surfaces 35" and 34" of the wedge shaped member 27" and the distal end 24" of the lever 22" such that the lever 22" pivots about the pivot point 25" to move the lever 22" away from the slider 26". This in turn moves the drive member 21 in the direction of arrow Y1 along axis Y which lies substantially perpendicular to axis X.

When current ceases to flow between the terminals 32" and 33" the resistance heating of the Nitinol muscle wire 30 is stopped and as the muscle wire cools the compression spring 29" causes the muscle wire 30 to once again deform under super elasticity and the slider 26" moves in the direction of arrow X1, causing rotation of the lever 22" about pivot point 25" and corresponding movement of the drive member 21 in the direction of arrow Y2. The movement of the lever 22" is therefore similar to the movement of the lever 22' described above.

The actuator 20" further comprises a return spring assembly 74 including a leaf spring 75 which contacts the lever 22" to bias the lever 22" towards the slider 26". The return spring assembly 74 ensures the distal end 24" of the lever 22" remains in contact with the wedge shaped member 27" at all times.

When the actuator 20" is installed in the pump part 2, the membrane 37 may provide a biasing function to the drive member 21 to bias the drive member 21 in the direction of arrow Y2. The membrane 37 applies a force in the direction of arrow Y2 throughout the full range of reciprocating motion of the drive member 21. When the Nitinol muscle wire 30 cools down and the slider 26" under the restoring force of the spring 29 returns to the first position against the end stop (not shown) the membrane 37 urges the drive member 21 to move in the direction of arrow Y2 forcing the lever 22" to pivot about pivot point 25". In this way the membrane 37 forms a part of the actuator 20". However, in other embodiments the membrane 37 may be omitted as the return spring assembly 74 may provide sufficient biasing force to ensure the distal end 24" of the lever 22" remains in contact with the wedge shaped member 27" at all times.

When the Nitinol muscle wire 30 is heated to cause the Nitinol muscle wire to contract and move the slider 26' in the direction of arrow X2, relative sliding movement between the inclined surfaces 34' and 35' occurs forcing the lever 22' to pivot about pivot point 25' and urging the drive member 21 to move in the direction of arrow Y1 to its fully extended position and stretching the membrane 37 (if present) to its full extent.

Figure 9:
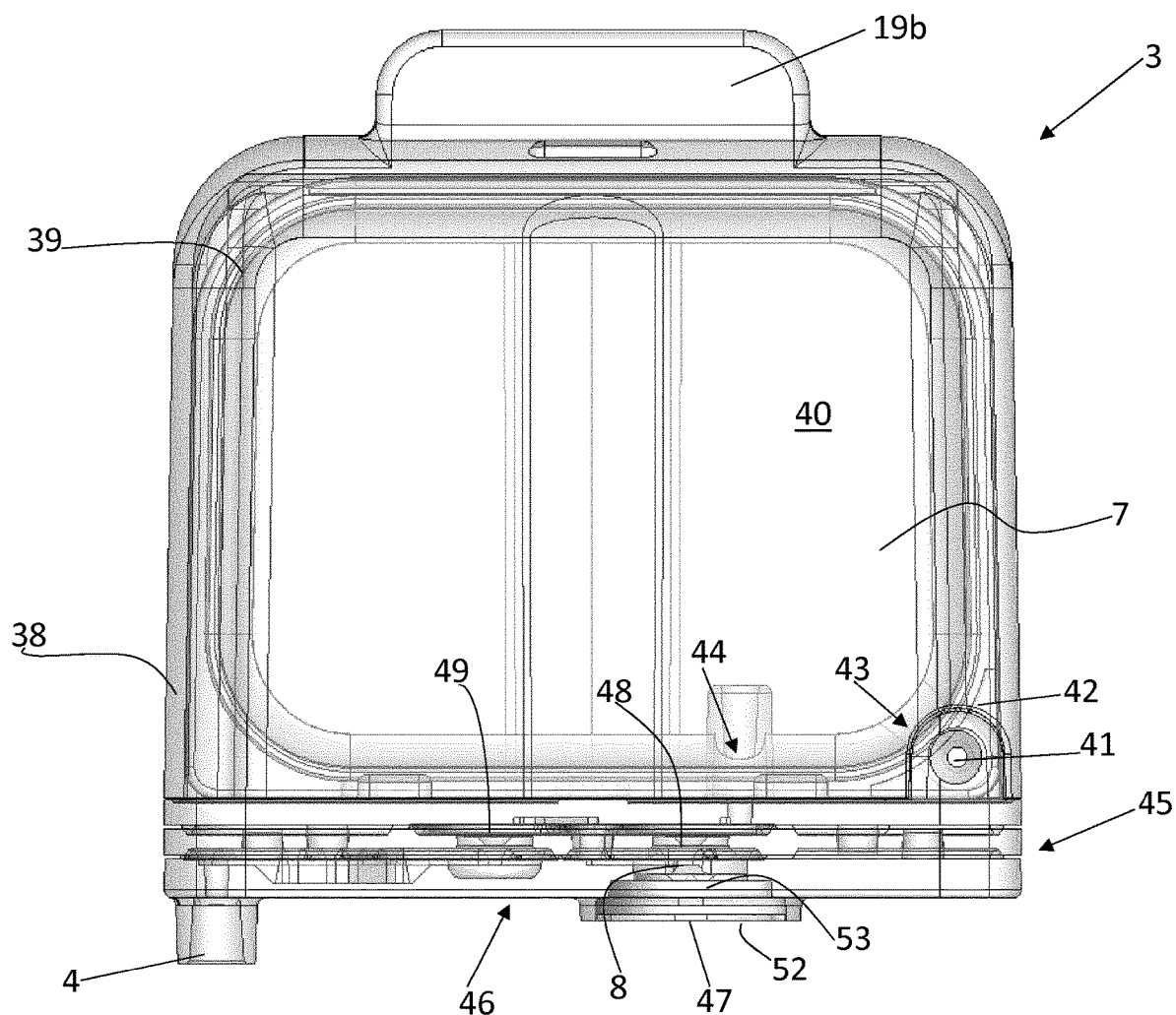
FIG. 9 shows a plan view of the cartridge.
Figure 10:
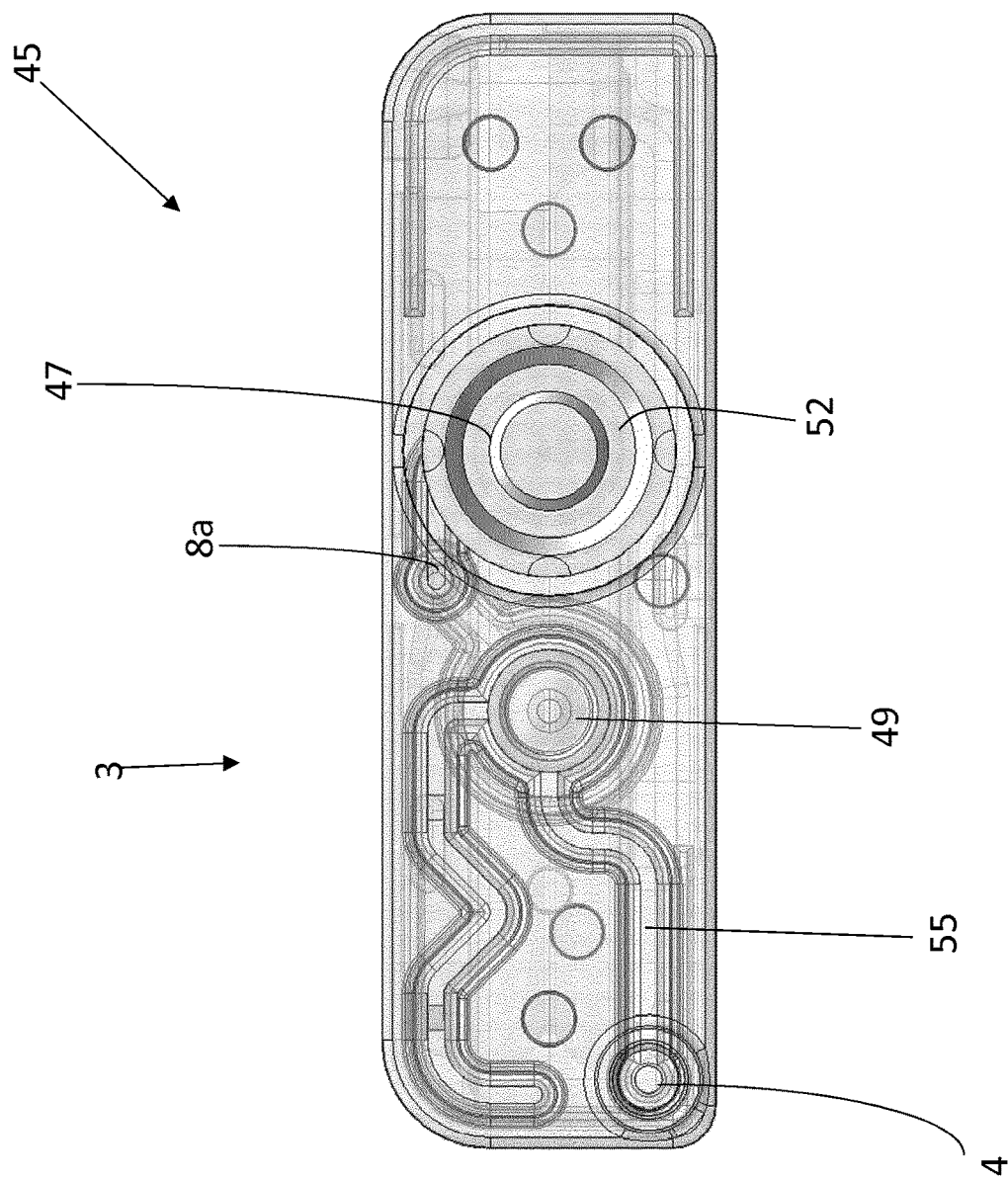
FIG. 10 shows a front view of the cartridge.
Figure 11:
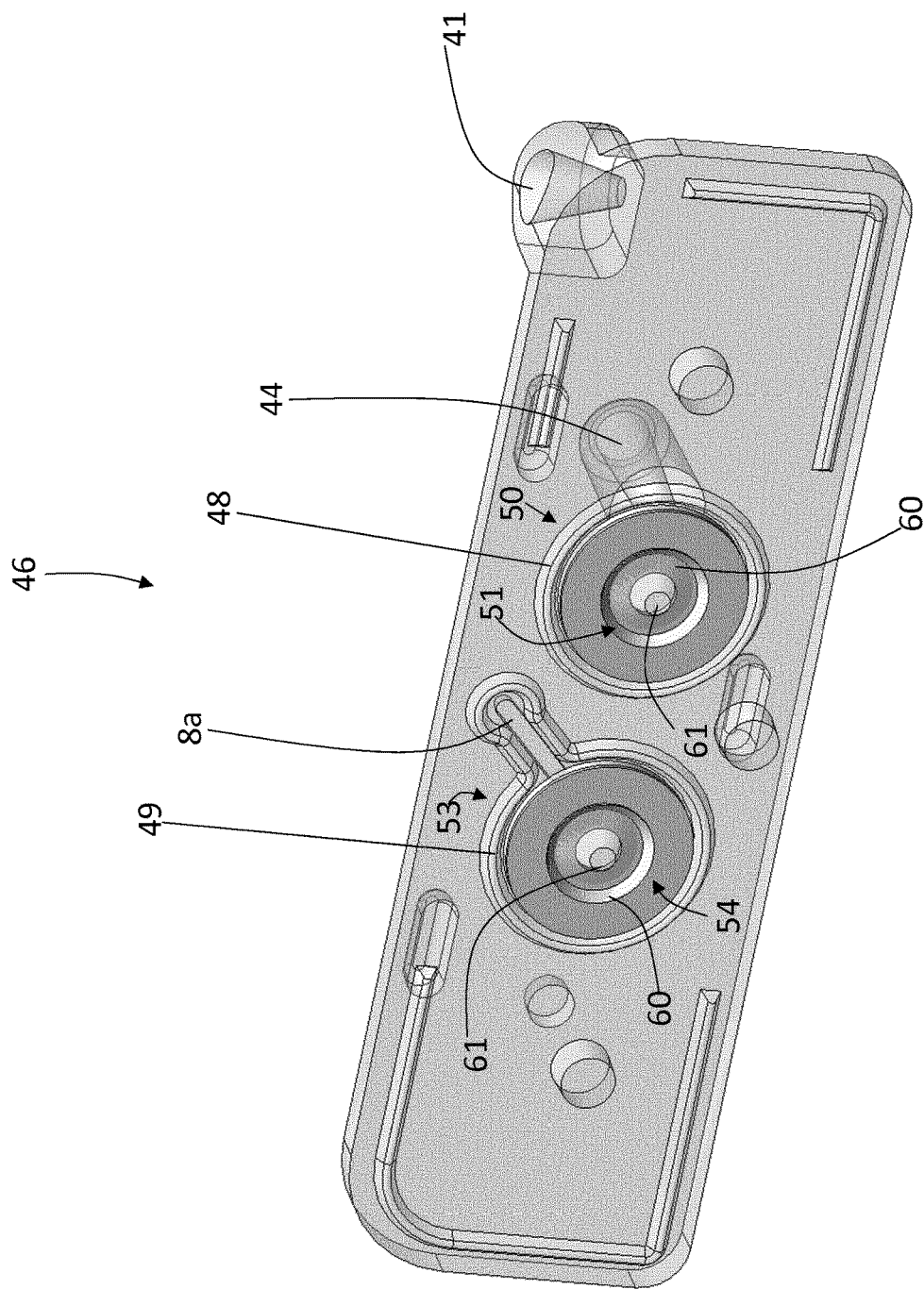
FIG. 11 shows in detail the inlet and outlet valves of the pumping chamber part of the cartridge.

Turning next to FIGS. 9 to 11 the cartridge 3 will now be described in detail. As shown in FIG. 9 the cartridge 3 includes a reservoir case 38 containing the reservoir 7 for storing a supply of insulin. The reservoir 7 is formed as a rectangular frame 39 with front and rear film covers welded onto the frame so as to bound the fluid volume of the reservoir 7. The reservoir 7 fits within the case 38 which provides structural support and protection for the reservoir 7.

At one corner the case 38 includes a filling aperture 41 for receiving a filling needle. Beneath the aperture 41 is a rubberised insert 42 which covers and seals an inlet port 43 of the reservoir 7 passing through the reservoir frame 39. The needle tip penetrates the seal member 42. By connecting a supply of insulin under positive pressure to the filling needle the insulin may be injected through the needle into the inlet port 43 of the reservoir 7 so as to fill the reservoir with insulin. The reservoir frame 39 also includes an outlet port 44 in fluid communication with a pump stack indicated generally by reference number 45.

The pump stack 45 includes a valve assembly 46, the pumping chamber 8 having a pumping chamber membrane 47 and the outlet port 4. FIG. 10 illustrates a front view of the cartridge 3 in detail showing the front face of the pump stack 45, and FIG. 11 illustrates the valve assembly 46 in more detail. The valve assembly 46 includes an inlet valve 48 and an outlet valve 49. The inlet valve 48 has an inlet side 50 fluidically connected via the inlet port 54 to the reservoir 7. Inlet valve 48 also has an outlet side 51 which opens into the pumping chamber 8. The pumping chamber membrane 47 has a front face 52 and a rear face 53, where the rear face 53 forms a boundary to the pumping chamber 8 such that the displacement of the membrane 47 changes a volume of the pumping chamber 8. The pumping chamber membrane 47 sits adjacent the outlet side 51 of the inlet valve 48.

The pumping chamber 8 also comprises a fluid passage 8a extending between the outlet side 51 of the inlet valve 48 and an inlet side 53 of the outlet valve 49. The outlet valve 49 also has an outlet side 54 fluidly connected via conduit 55 to the outlet port 4.

The inlet valve 48 and the outlet valve 49 are each one-way check valves and include an annular elastomeric valve member 60 over a conical valve seat 61 such that the conical valve seat 61 projects through the hole in the centre of the annular valve member 60. The outer periphery of the valve member 60 is fixed—by bonding or clamping, for example—within the pump stack 45. The conical valve seat 61 is projected through the hole in the valve member 60 so that the inner periphery of the elastomeric valve member is deflected by the valve seat 61 and the valve seat 61 forms a seal around the inner periphery of the annular valve member. More particularly, the conical valve seat 61 seals onto an edge of the inner periphery of the hole in the annular valve member.

The sealing is sufficient to prevent flow of fluid from the inlet side to the outlet side of the respective valve unless the pressure on the inlet side is higher that the pressure on the outlet side and the difference exceeds the breakthrough pressure of the valve by providing sufficient force to partially and temporarily lift the valve membrane 60 away from the valve seat 61. The force required to lift the valve member 60 away from the valve seat 61 is the extent to which the valve member 60 is deflected by the valve seat 61, the stiffness of the elastomeric valve seat 60 and the surface finish on the valve seat 61. By carefully combining these features, micro valves can be fabricated with different breakthrough pressures.

During filling of the reservoir 7 with fluid, in this case insulin, the fluid is injected under positive pressure sufficient to exceed the breakthrough pressure of the inlet valve 48, which may be set at approximately 100 millibars. In practice, the breakthrough pressure may be in the range of approximately 10 to approximately 500 millibars. This equates to a relatively low tension in the elastomeric valve member 60 of typically less than 1 Newton.

When the pressure in the reservoir 7 during filling exceeds the breakthrough pressure of the inlet valve 48, fluid flows from the reservoir 7 through the reservoir outlet port 44 and into the pumping chamber 8 and starts to build pressure on the inlet side of the outlet valve 49. Once the positive pressure differential between the inlet side and the outlet side of the outlet valve 49 exceeds the breakthrough pressure of the outlet valve 49 the outlet valve 49 opens and fluid passes via conduit 55 to the outlet port 4 of the cartridge 3. With the infusion tube 6 and infusion set 5 connected to the outlet port 4 of the cartridge 3 insulin flows to the infusion set 5 expelling air in the infusion tube 6 and the infusion set 5 until the insulin begins to exit the infusion set 5 indicating that the reservoir 7 is full and the infusion set 5 is primed ready for use.

At this point the injection of insulin through the filling needle into the filling aperture 41 can be stopped, and the pressures in the reservoir 7 will return to ambient causing the inlet valve 48 and the outlet valve 49 to close leaving a positive pressure in the valve apparatus 46. Removal of the filling needle from the filling aperture 41 causes the seal insert 42 to seal the reservoir 7 to prevent escape of insulin from the filling aperture 41. The filled and primed cartridge 3 having the infusion set 5 connected is now ready for coupling to the pump part 2.

As explained above the drive member 21 of the actuator 20, 20' or 20" rests in either a fully extended position or a fully retracted position in the Y direction. Upon installation of the cartridge 3 in the pump part 2 the aperture membrane 37 (where provided) or the head 38 of the drive member 21 directly contacts the front face 52 of the pumping chamber membrane 47.

By successively energising the Nitinol muscle wire 30 the drive member 21 of the actuator 20, 20' or 20" is caused to move in reciprocating motion in the direction of arrows Y1 and Y2 along axis Y which, by displacement of the pumping chamber membrane 47, causes successive opening and closing of the inlet valve 48.

Retraction of the drive member 21 in the direction of arrow Y2 causes the pumping chamber membrane 47 to partially relax out from the pumping chamber which increases the volume of the pumping chamber and thereby decreases the pressure in the pumping chamber 8 such that the positive pressure differential between the inlet side 50 and the outlet side 51 of the inlet valve 48 increases above the breakthrough pressure of the inlet valve so that the inlet valve 48 opens and the pumping chamber 8 fills with insulin from the reservoir 7.

Extension of the drive member 21 in the direction of arrow Y1 stretches the pumping chamber membrane 48 into the pumping chamber which decreases the volume of the pumping chamber 8 and thereby increases the pressure in the pumping chamber 8 until the positive pressure differential between the inlet side 53 and the outlet side 54 of the outlet valve 49 increases above the breakthrough pressure of the outlet valve 49 whereby the outlet valve 49 opens and insulin flows through the outlet valve and via the outlet port 4 to the infusion set 5 for delivery of insulin to the patient.

Using the handset 10 the control electronics in the circuit board 13 of the pump part 2 may be controlled to activate the actuator 20, 20' or 20" to provide the required delivery profile of insulin to the patient.

The cartridge 3 may be exchanged for a full cartridge when empty and refilled as described above.

Although the invention has been described above with reference to one or more preferred embodiments, it will be appreciated that various changes or modifications may be made without departing from the scope of the invention as defined in the appended claims.

The invention claimed is:

1. An actuator for a pump, the actuator comprising:
 a wedge shaped member arranged to move in substantially linear reciprocating motion;
 a drive member operatively coupled to the wedge shaped member, the wedge shaped member being arranged to deflect the drive member as the wedge shaped member moves; and
 a shape memory material having a first end and a second end, the first end being electrically connected to a first electrical connection terminal and being fixed with respect to the first electrical connection terminal, the second end being electrically connected to the wedge shaped member and being fixed with respect to the wedge shaped member, and the wedge shaped member comprising electrically conductive material that is electrically connected between a second electrical connection terminal and the second end of the shape memory material.

2. The actuator according to claim 1, wherein the wedge shaped member is moveable with respect to the drive member.

3. The actuator according to claim 2, wherein the wedge shaped member and the drive member are arranged to convert reciprocating substantially linear motion of the wedge shaped member along a first axis to reciprocating substantially linear motion of the drive member along a second axis substantially perpendicular to the first axis.

4. The actuator according to claim 1, wherein the wedge shaped member has a first surface, a second surface, and a third surface between the first surface and the second surface, wherein the third surface is inclined with respect to the first surface and the second surface.

5. The actuator according to claim 1, wherein the actuator further comprises a lever rotatable about a pivot point, and the drive member is operatively coupled to the lever.

6. The actuator according to claim 5, wherein the lever has a distal end opposite the pivot point, and the distal end of the lever is operatively coupled to the wedge shaped member.

7. The actuator according to claim 6, wherein the wedge shaped member has a first surface, a second surface, and a third surface between the first surface and the second surface, wherein the third surface is inclined with respect to the first surface and the second surface, and wherein the distal end of the lever has an inclined surface arranged for sliding contact along the third surface of the wedge shaped member.

8. The actuator according to claim 5, further comprising a first biasing element for biasing the lever towards the wedge shaped member about the pivot point.

9. The actuator according to claim 5, wherein the lever provides the electrical connection between the wedge shaped member and the second electrical connection terminal.

10. The actuator according to claim 1, further comprising a runner, wherein the wedge shaped member is arranged to move in sliding contact with respect to the runner.

11. The actuator according to claim 1, further comprising a runner, wherein the wedge shaped member is arranged to move in sliding contact with respect to the runner, and wherein the runner provides the electrical connection between the wedge shaped member and the second electrical connection terminal.

12. The actuator according to claim 1, further comprising a second biasing element for biasing the wedge shaped member to a first position.

13. The actuator according to claim 1, further comprising a second biasing element for biasing the wedge shaped member to a first position, wherein the second biasing element provides the electrical connection between the wedge shaped member and the second electrical connection terminal.

14. The actuator according to claim 12, wherein the second biasing element is a coil spring, and the shape memory material passes through an eye of the coil spring.

15. The actuator according to claim 1, wherein the shape memory material has a first shape corresponding to a first position of the wedge shaped member, and a second shape corresponding to a second position of the wedge shaped member.

16. The actuator according to claim 1, wherein the shape memory material is a resistance heating shape memory alloy.

17. The actuator according to claim 1, wherein the shape memory material is a wire.

18. The actuator according to claim 17, wherein the wire is substantially straight between the first end and the second end.

19. A pump comprising:
- a pumping chamber having a volume with an inlet, an outlet, and a membrane the displacement of which changes the pumping chamber volume; and
- an actuator according to claim 1, wherein the drive member is operatively coupled to the pumping chamber membrane.

20. An infusion system for infusion of a liquid therapeutic product, the infusion system comprising:
- a reservoir for storing the liquid therapeutic product; and
- the pump according to claim 19.

21. The actuator according to claim 1, wherein the shape memory material is a shape memory alloy.

22. The actuator according to claim 1, wherein the shape memory material is a Nitinol alloy.

* * * * *